(12) United States Patent
Mrochen et al.

(10) Patent No.: US 8,475,437 B2
(45) Date of Patent: Jul. 2, 2013

(54) RADIATION SYSTEM FOR OPTHALMOLOGICAL APPLICATIONS

(75) Inventors: Michael Mrochen, Eglisau (CH);
Michael Büeler, Zürich (CH); Urs Schelling, Zürich (CH)

(73) Assignee: IROC Innocross AG, Zug (CH)

( * ) Notice: Subject to any disclaimer, the term of this patent is extended or adjusted under 35 U.S.C. 154(b) by 841 days.

(21) Appl. No.: 12/307,038

(22) PCT Filed: Jun. 28, 2007

(86) PCT No.: PCT/EP2007/005740
§ 371 (c)(1),
(2), (4) Date: Nov. 12, 2009

(87) PCT Pub. No.: WO2008/000478
PCT Pub. Date: Jan. 3, 2008

(65) Prior Publication Data
US 2010/0069894 A1    Mar. 18, 2010

(30) Foreign Application Priority Data

Jun. 30, 2006  (DE) .......................... 10 2006 030 219

(51) Int. Cl.
*A61B 18/18* (2006.01)
*A61B 3/10* (2006.01)
*A61F 9/008* (2006.01)
*A61B 3/12* (2006.01)

(52) U.S. Cl.
CPC ....... *A61F 9/008* (2013.01); *A61F 2009/00872* (2013.01); *A61B 3/1225* (2013.01)
USPC .................................. 606/4; 606/5; 351/221

(58) Field of Classification Search
CPC   A61F 9/008; A61F 2009/00872; A61B 3/1225
USPC ................. 606/4–6; 351/112, 247, 205, 206, 351/212, 216, 221
See application file for complete search history.

(56) References Cited

FOREIGN PATENT DOCUMENTS

WO        WO93/16631    *  9/1993    ........................ 606/5

* cited by examiner

*Primary Examiner* — Huy K Mai
(74) *Attorney, Agent, or Firm* — John C. Pokotylo; Straub & Pokotylo (57) ABSTRACT

An irradiation system for opthalmological applications includes: a radiation source (1) for changing the biomechanical properties of the cornea; an optical system for directing the radiation towards the tissue; a beam-splitter (3) which couples out a part of the radiation directed towards the tissue for measuring or monitoring purposes; the beam-splitter also being set up in order to combine a further radiation of a different wavelength with the first-mentioned radiation; a controller for controlling the system, including a sensor; a mechanical stand (16) for supporting an irradiation unit (17); and interfaces for exchange of data.

11 Claims, 14 Drawing Sheets

RADIATION SYSTEM FOR OPTHALMOLOGICAL APPLICATIONS

SUMMARY OF THE INVENTION

The invention relates to an irradiation system for opthalmological applications for the purpose of achieving changes in the biomechanical properties of components of the eye, particularly of the cornea. For this purpose, the present invention employs an electromagnetic radiation designated here as 'primary radiation', preferably within the spectral range from 300 nm to 800 nm: This radiation is preferably generated with LEDs or laser diodes. The electromagnetic radiation designated here as 'primary radiation' is not intended to bring about any so-called photoablative effect—that is to say, an effect with which tissue is removed from the eye, as occurs in the case of a reshaping of the cornea, for example in accordance with the LASIK procedure. Rather, the primary radiation according to the invention serves to change the tissue, in particular the cornea, as regards its biomechanical properties without removing tissue. A change in the biomechanical properties, of the cornea for example, obtains when the tissue is changed in its elasticity ('hardens'). For this purpose the state of the art is familiar with so-called photosensitisers—that is to say, active substances—which are injected into the tissue and which promote there the stated effect of the change in biomechanical properties of the tissue. As a result, the primary radiation according to the invention accordingly brings about a biomechanical stabilisation of the cornea.

For this purpose the invention provides an irradiation system of the initially stated type, exhibiting the following components:

a. at least one radiation source for a primary radiation, which emits electromagnetic radiation within the range from 300 nm to 800 nm which in the irradiated tissue brings about, photochemically and/or photophysically, a change in the biomechanical properties, particularly of the cornea, b. an optical system with at least two lenses and devices, in order to direct the radiation at a predetermined distance towards the tissue to be irradiated, wherein means are provided in order to adjust a temporally and/or spatially variable intensity distribution of the radiation, c. at least one diaphragm which is designed and arranged in such a way that together with the optical system it generates a predetermined irradiation region, d. at least one beam-splitter which couples out a part of the radiation directed towards the tissue for measuring or monitoring purposes and/or is set up for observation purposes and/or for real-time diagnosis and/or for bringing the stated radiation together with a further radiation of a different wavelength from a further radiation source, e. a controller for controlling or regulating at least one of the radiation sources, including at least one sensor for, for example, the current consumption of the radiation source, the temperature of one or more components of the system, the temperature of the environment, or the atmospheric humidity of the environment, f. an electrical power pack for supplying power to the irradiation system, g. a mechanical stand for supporting an irradiation unit which includes at least the components named in features a., b., c., d., in relation to the tissue to be irradiated, h. a display device for displaying data that are relevant for the irradiation system, such as the emission of radiation, treatment parameters or possible misadjustments, i. an electronic interface between the controller and an external computer for the purpose of transmitting data such as, for example, duration of irradiation, dose, light distribution, measured data, data from databases, and j. an interface or an input device for the input of data by a user, such as, for example, irradiation times or irradiation dose.

LEDs, thermal light-sources with associated filters, or lasers are preferably employed as radiation sources in the irradiation system described above.

Further configurations of the invention are described in the further claims and in the following description of embodiments with reference to the Figures.

DETAILED DESCRIPTION

Figure 1:
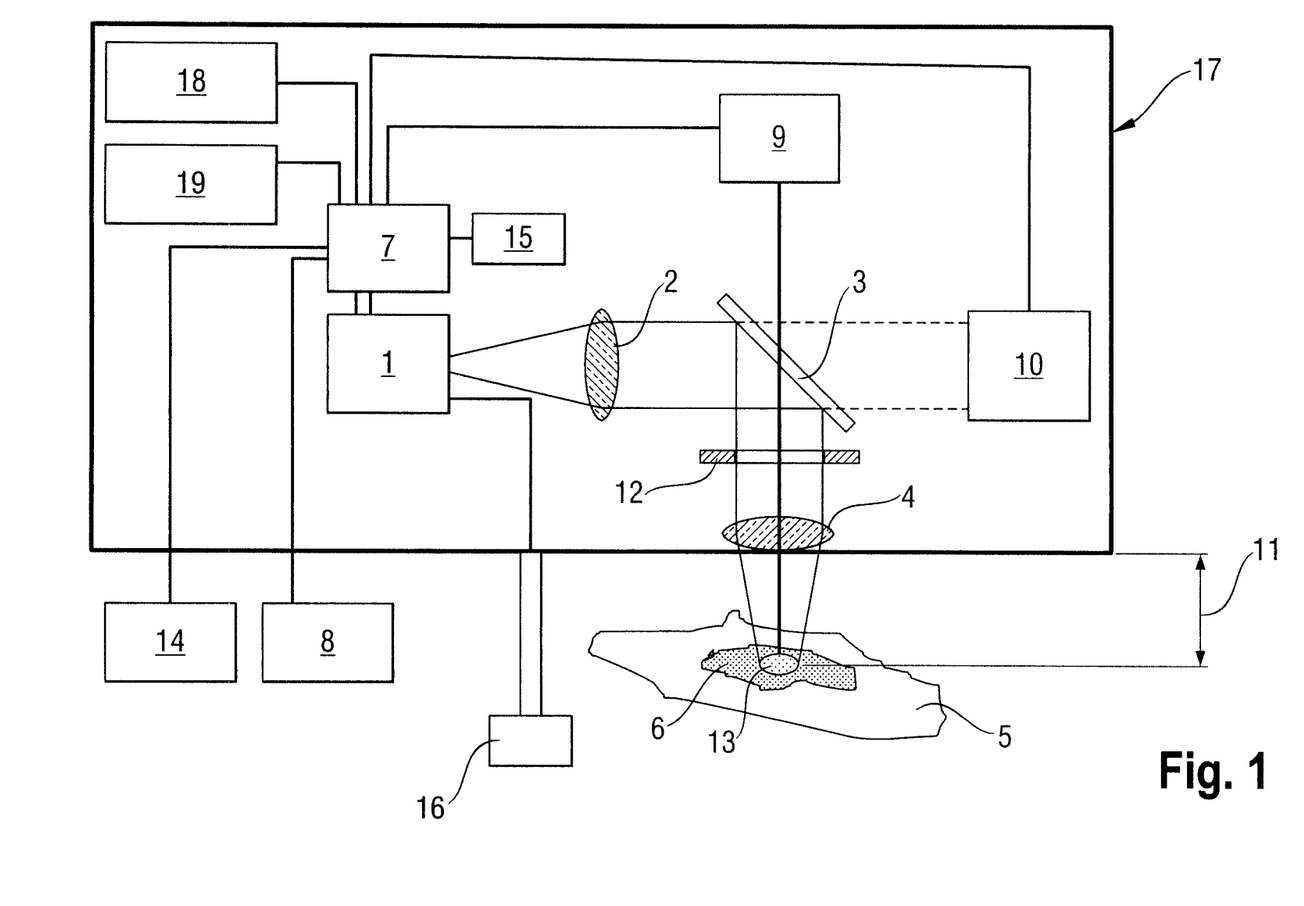
FIG. 1 schematically, an irradiation system for medical applications.

The irradiation system for medical purposes according to FIG. 1 exhibits a radiation source 1 for electromagnetic radiation, for example an LED, a laser, or a thermal light-source. The radiation is focused onto tissue 5 to be treated via a lens 2 and a semitransmitting mirror 3 as well as a further lens 4.

The embodiments of the invention described here are suitable, in particular, for opthalmological use of the irradiation system.

An active substance that enables or promotes the photochemical and/or photophysical effects of the radiation introduced into the tissue has been introduced into the tissue 5 to be treated.

The irradiation region is denoted by reference symbol 13.

An irradiation unit 17 is supported on a stand 16 in such a way that a predetermined distance 11 is adjustable between the optical element 4 of the irradiation unit 17 arranged last in the radiation path and the tissue 5 to be irradiated.

With the beam-splitter 3 varying functions can alternatively be obtained:

On the one hand, with the beam-splitter 3 a part of the radiation emitted from the radiation source 1 can be coupled out and supplied to a measuring device 10 which, for example, measures the energy and/or the intensity distribution and/or the time distribution of the radiation.

On the other hand, with the beam-splitter 3 a part of the radiation reflected back from the tissue 5 can also be supplied to an observation device 9.

According to a third variant, with the beam-splitter 3 the radiation emitted from the radiation source 1 can be combined with a further radiation, the further radiation then being emitted from a further radiation source which is arranged in the structural element provided with reference symbol 9. The further radiation then preferentially has a different wavelength from that of the radiation emitted from the radiation source 1.

A controller 7 serves for controlling, inter alia, the stated components 1, 10 and 9.

The controller 7 receives data from a sensor 15 which registers important parameters of the irradiation system, such as, for example, the current consumption of the radiation source, temperatures of the system and/or of the environment, the atmospheric humidity of the environment and further quantities.

A power pack 14 serves for supplying power to the irradiation unit 17.

A display element 18 serves for displaying parameters of interest, such as the emission of light, treatment parameters of interest with respect to the patient, or even possible errors arising.

An interface 8 is connected to the controller 7 and serves for connecting the same to an external computer (not shown) for the purpose of transmitting data that are relevant for the treatment, such as, for example, the durations of irradiation, the irradiation dose, the light distribution, measured data of interest, or even for transmitting data from a database.

An interface 19 may be provided for the purpose of communicating data to the controller 7 and, in particular, for connecting a PC to input devices for the user with respect to the details of the treatment.

Figure 3:
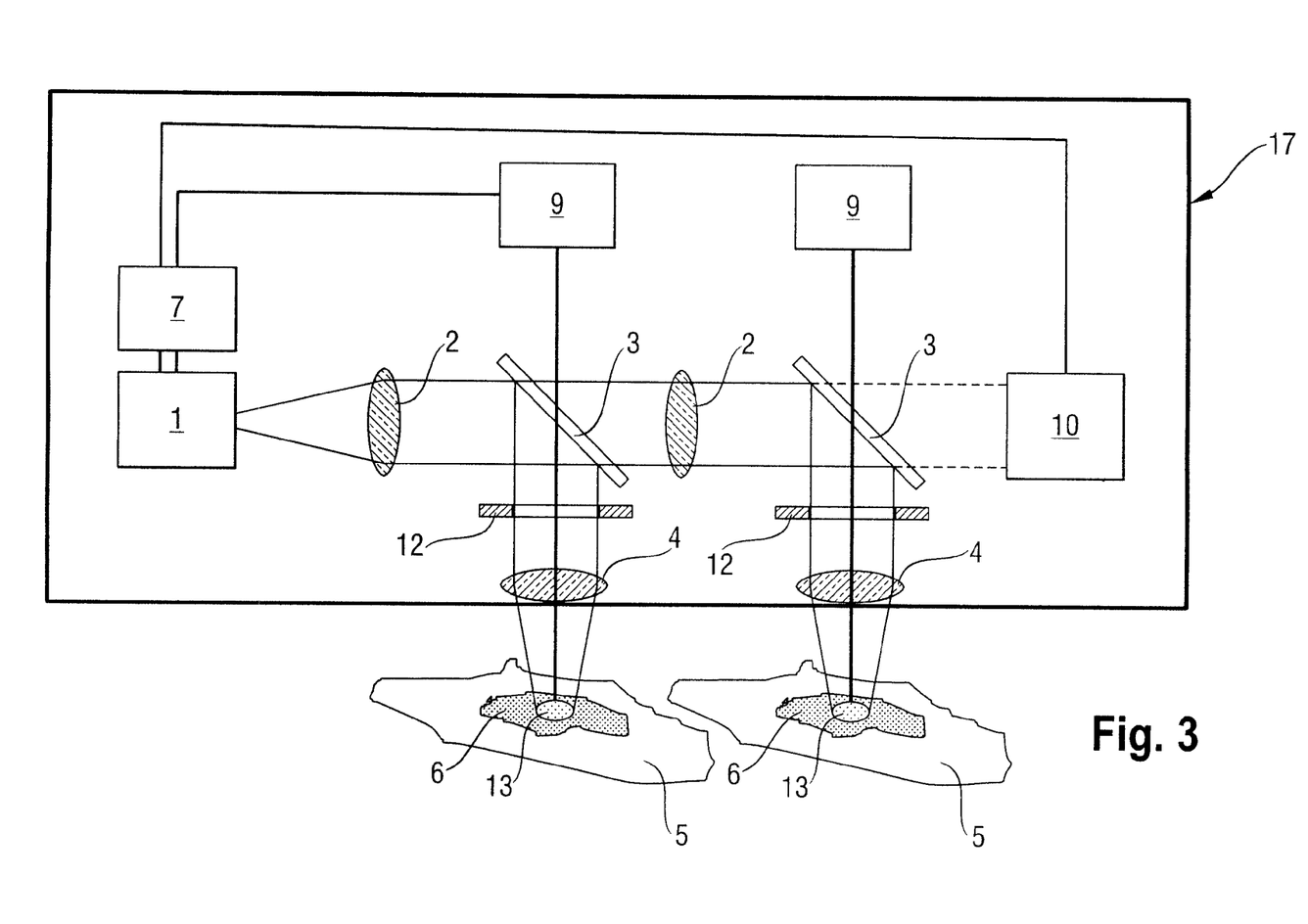
FIG. 3 a further embodiment of an irradiation system for medical purposes, with two subsystems.

Structural elements that correspond to one another or that are functionally similar are provided with the same reference symbols in the Figures. Note that in a further embodiment of an irradiation system depicted in FIG. 3, two subsystems may collectively include two (2) lenses 2, two (2) beam splitters 3, two (2) further lenses 4, two (2) diaphragms 12, and two (2) observation means 9, to irradiate two regions of tissue 5, each provided with active substance 6, at two areas 13.

Figure 2:
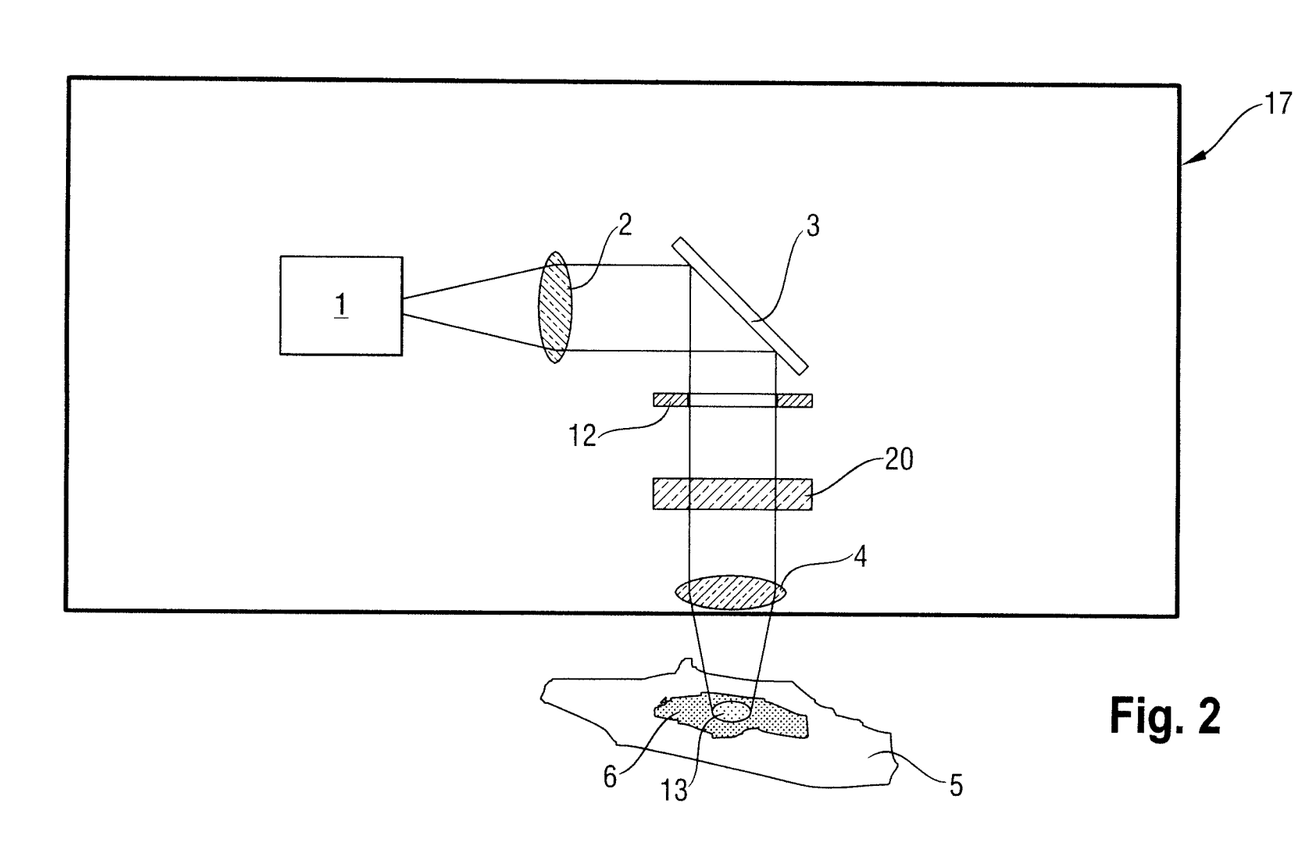
FIG. 2 a detail of the irradiation system.

FIG. 2 shows a detail of the irradiation system represented in FIG. 1, wherein in the treatment unit 17 in the beam path upstream of the lens 4 an optical element 20 is arranged which has a diffractive or holographic effect, in order to generate a predetermined and selectable light distribution in the irradiation region 13.

In modification of the embodiment described above, the optical element 20 may also be a temporally variable light modulator, for example a liquid-crystal modulator, in order to generate a selectable light distribution in the irradiation region 13.

In modification of the embodiments described above, the optical element 20 may also generate an adjustable and variable light distribution in the tissue 5 by movement in space.

Figure 14:
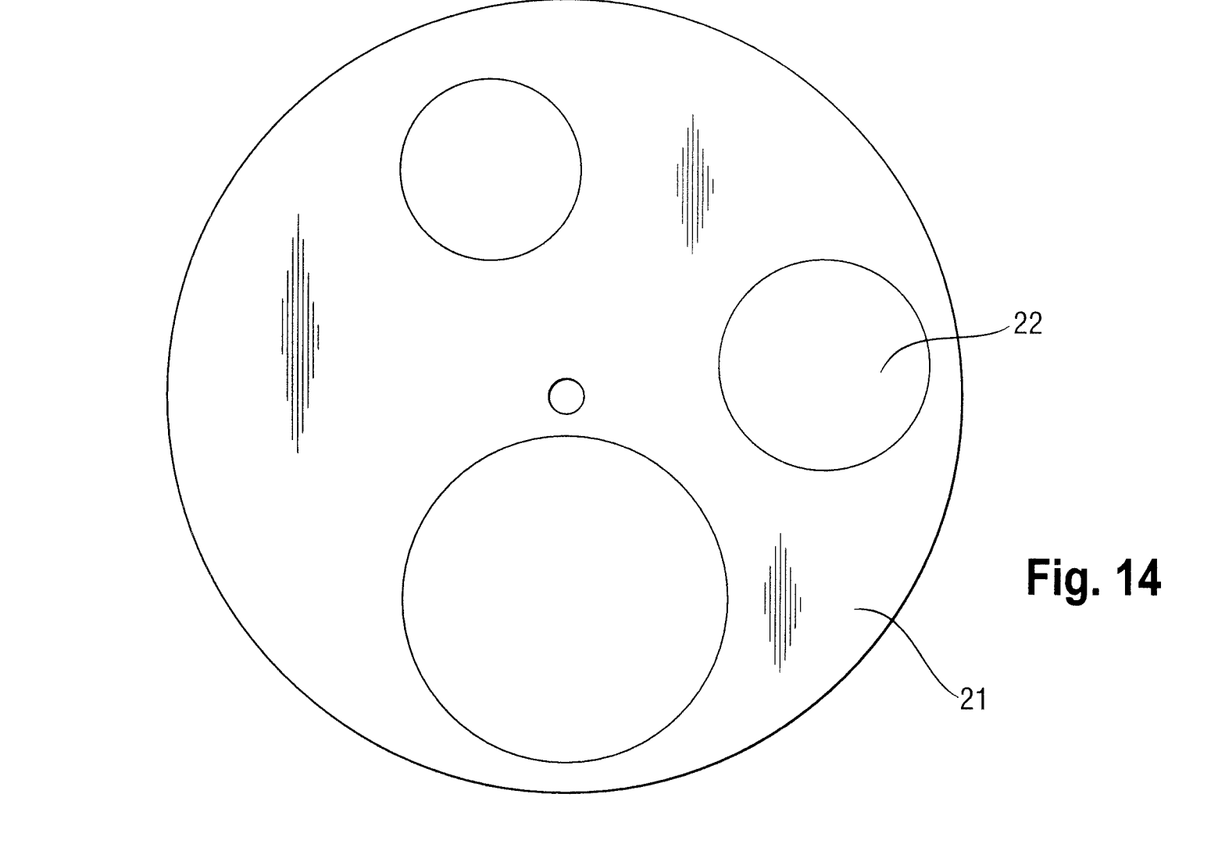
FIG. 14 a device for exchanging optical elements.

According to a further variant, there may be provision to arrange at the position of the optical element 20 a change gear (revolver) 21—shown in FIG. 14—with which varying optical elements—such as, for example, absorbers 22—are capable of being moved into the radiation path, in order to generate a predetermined light distribution in the radiation region 13. In this case a chemical active substance 6 (FIG. 2) has been introduced into the region of the tissue 5 to be irradiated, in order to enable or at least promote the physical or chemical effect of the radiation. Such chemical active substances are known as such.

Figure 12:
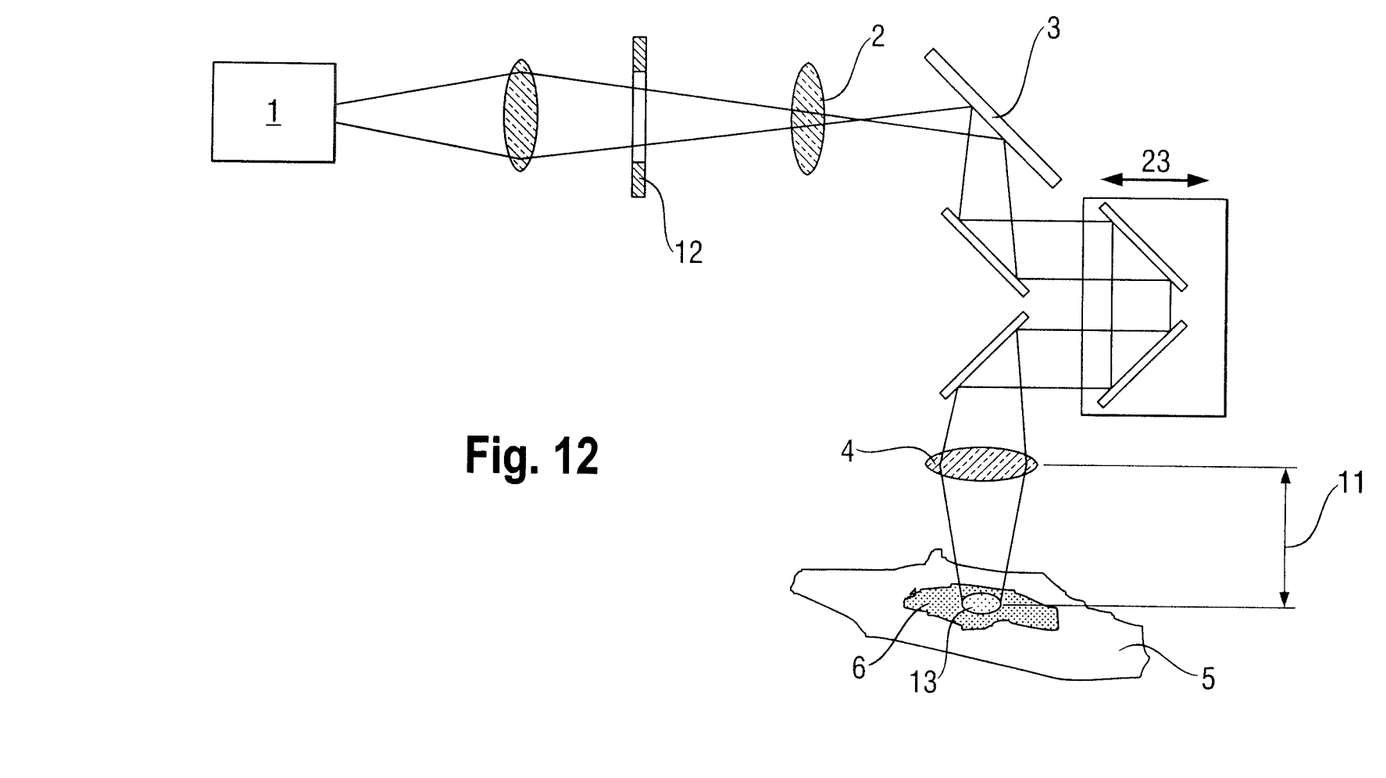
FIG. 12 a variant of the embodiment shown in FIG. 11.
Figure 13:
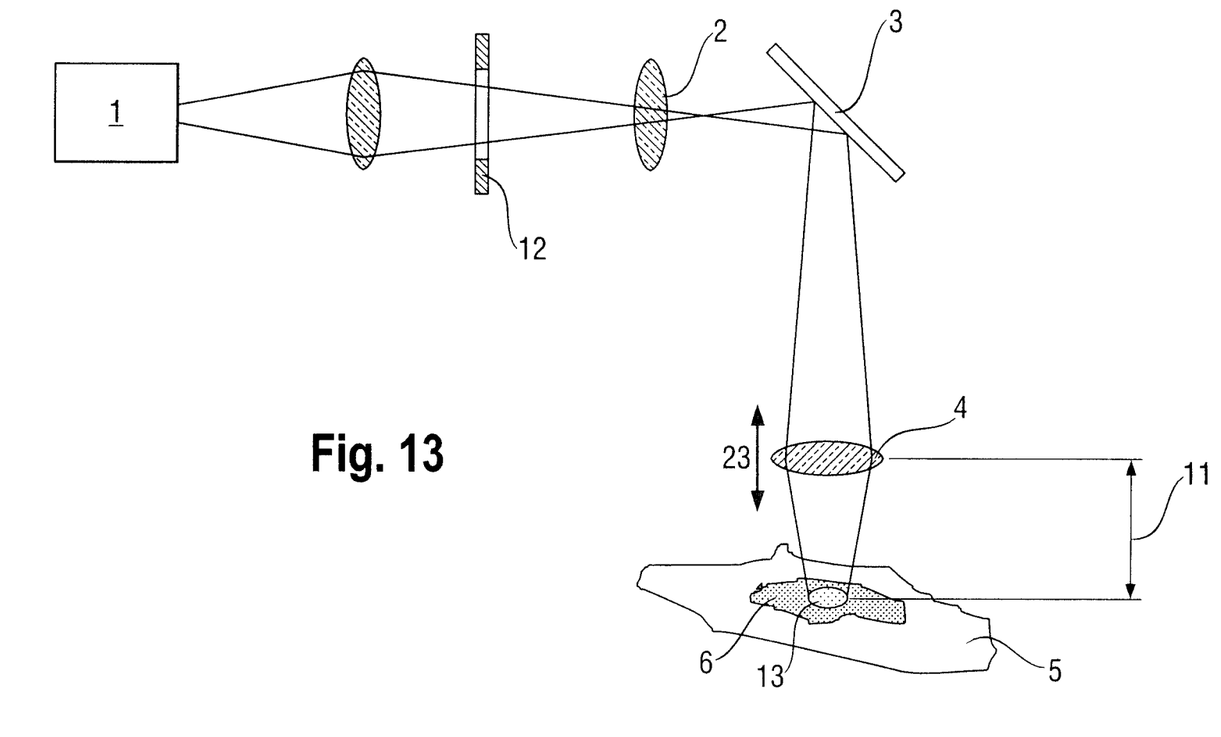
FIG. 13 a variant of FIG. 12.

FIGS. 12 and 13 show modifications of the embodiments described above, wherein optical elements, as indicated by the arrow 23, are displaceable in space, in order to adjust the light distribution in the irradiation field 13.

These embodiments also enable the distance 11 between the irradiation unit 17 and the tissue 5 to be irradiated to be adjustable.

The diaphragm 12 shown in FIG. 1 is preferentially controllable (adjustable) as regards its diaphragm aperture and/or with regard to its distance in relation to the other optical elements.

According to a variant, the diaphragm 12 may be configured as a rotating mask in such a manner that differing regions of the beam are masked out by the rotating diaphragm (mask) in each instance in the course of rotation, so that a temporally and spatially varying radiation dose on the tissue 5 occurs. For instance, a helical mask generates a parabolic light distribution in the radiation region 13.

The irradiation system will be described in more detail in the following with regard to the diagnostic means optionally provided in the block 9:

The measuring means 9 may, for example, be an instrument for optical coherence tomography. The measuring instrument 9 may optionally also be an instrument for measuring the optical length of the eye, or a measuring means for ascertaining the topography of the cornea in real time.

Another configuration provides that the measuring means 9 is a wavefront-diagnosis system for measurement in real time of the wavefront that is reradiated from the tissue 5.

The measuring means 9 may optionally also be a Scheinpflug camera.

Another configuration provides that the measuring means 9 is a video system for imaging. The measuring means 9 may also be a camera system for electronic imaging.

A further configuration provides that the measuring means 9 is a microscope for visual observation of the treatment.

On the other hand, the measuring means 9 may be a spectrometer for fluorescence analysis.

On the other hand, in another configuration the measuring means 9 may be a system for registering the movements of the eye (so-called eye tracker).

Another configuration provides that the measuring means 9 is an instrument for measuring the thickness of the cornea and/or of the epithelium.

The measuring means 9 may also be an instrument for distance measurement from the eye (relative to the optical components).

In the following, varying functions of the beam-splitter 3 according to varying embodiments of the invention will be elucidated:

As already indicated above, in a first variant of the invention the beam-splitter 3 serves to combine a radiation of a different wavelength with the radiation coming from the radiation source 1 (so-called primary radiation), the radiation source for the second radiation (secondary radiation) being seated in the block denoted by 9. In the case of the secondary radiation, it may be a question, for example, of radiation with a wavelength that is suitable for UV photoablation of corneal tissue.

According to another variant of the invention, the secondary radiation may be selected in such a way that it achieves a fluorescence effect in the irradiated tissue, devices then being provided in order to evaluate the fluorescence radiation.

A further variant of the use of the beam-splitter 3 provides that the secondary radiation has a wavelength that is suitable to thermally excite the tissue 5 to be irradiated and in this way to promote the desired effects.

A further variant of the function of the beam-splitter 3 is a secondary radiation which has been selected in such a way that it lies within the visible optical region (visible for the patient) and serves as so-called fixation beam or target beam.

According to another variant, the beam-splitter 3 serves to split up the primary radiation into two beam paths, so that a (smaller) beam part can be input into a measuring device 10 for measuring purposes. In this case, the signal of the measuring device 10 is passed to the controller 7 for processing.

Figure 11:
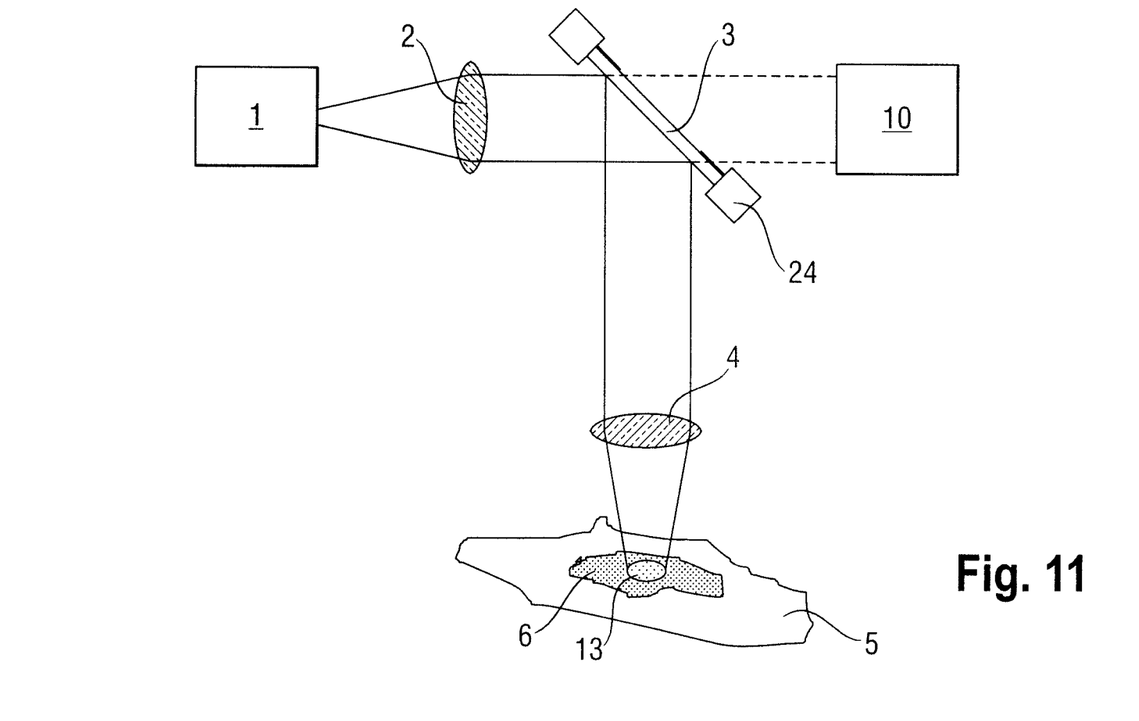
FIG. 11 a treatment system with adjusting devices for optical components.

According to another variant, the beam-splitter 3 is capable of being moved by electrically drivable means 24—see FIG. 11—in such a way that the irradiation region 13 can be guided (scanned) over the tissue 5.

In the following, details of the controller 7 will be elucidated:

The controller 7 may be designed in such a way that it emits the stated primary radiation in temporally pulsating manner or continuously.

The controller 7 may also be programmed in such a way that the power of the primary radiation is adjustable in temporally varying manner. In this case a special configuration provides that the power of the primary radiation emitted by the source 1 before an actual start of treatment is held below a predetermined threshold value over a predetermined time interval, in order to carry out adjustments or measurements with the radiation within this predetermined time interval. After the time interval, the radiation can then be raised above the stated threshold value, in order to achieve a desired chemical and/or physical effect.

The controller 7 may be capable of being controlled via a foot pedal for the purpose of emitting the radiation. It is also possible to operate the controller 7 via a remote control for the purpose of emitting the radiation.

If several radiation sources—for example, several LEDs—are provided for generating the primary radiation, the controller 7 can drive individual radiation sources in each instance, in order to control a desired spatial and/or temporal intensity progression of the radiation.

The block 10—indicating, in particular, a measuring device—according to FIG. 1 is, in particular, a photodetector with which the radiation dose per unit time and over the temporal progression of the treatment is measured. In this case there may be provision that a signal is passed by the measuring device 10 to the controller 7, in order to control the temporal progression of the radiation in the treatment plane in accordance with a predetermined program. If deviations arise with regard to a measured parameter in comparison with the set progression of the program, the controller 7 can change the radiation in such a way—in the manner of a closed control loop—that the stated parameter again lies within the set range.

If the block 9 in FIG. 1 denotes a so-called eye tracker; an appropriate signal concerning the movement of the eye can then be passed to the controller 7 (in the Figures the connecting lines between the functional blocks indicate the reciprocal exchange of data), and the controller 7 can then actuate a motor 24 (FIG. 11), in order to guide the movable beam-splitter 3 in a manner corresponding to the movement of the eye.

According to a further embodiment, the controller 7 is designed in such a way that it drives the movable stand 16 and in this way adjusts the position of the irradiation unit 17 in relation to the tissue 5.

The controller 7 is programmed in such a way that it takes account of data received from, for example, a computer via an interface, in particular with respect to the thickness of the cornea, the thickness of the epithelium, the riboflavin concentration (the latter is an example of an active substance 6 in the tissue 5), in order to ascertain optimal values for the treatment with regard to the dose and the temporal progression of the intensity, and then to control the system correspondingly.

In similar manner, the controller 7 can also evaluate measured data received via an interface with regard to optical parameters—that is to say, in particular with regard to the wavefronts and the topography—in order to ascertain optimal treatment data and to control the system correspondingly.

Analogously use may also be made of pre-operative and post-operative measured data, in order to compute optimal radiation parameters for the treatment.

The computation of data in the controller 7 is preferably effected in real time (online).

In the following, some configurations of the stand will be elucidated:

The stand 16 (FIG. 1) serves generally for positioning the irradiation unit 17 in relation to the tissue to be irradiated. For example, it may be a question of a table stand. For this purpose the stand may exhibit a spring-articulation arm—that is to say, an arm that is biased via springs in an initial position by way of rest position and that is capable of being swiveled out of this initial position by a user and then capable of being locked in the swiveled position. It is also possible to configure the mechanical stand 16 in such a way that it is capable of being positioned by means of electric motors, one-dimensionally, two-dimensionally or three-dimensionally.

It is also possible to connect the stand 16 directly to a patient's bed or a patient's chair.

In the following, some properties of the user interface 19 will be elucidated:

The user interface 19 enables, in particular, the input of the temporal and spatial progression of the radiation intensities. In this connection, in particular a progression of the intensity distribution is provided that is variable over time.

Moreover, the user interface 19 enables the input of patient data such as cornea thickness, epithelium thickness, concentration and type of the active substance 6 in the tissue, said active substance also being designated as 'photosensitiser'. Optical measured data can also be input via the user interface 19.

Figure 10:
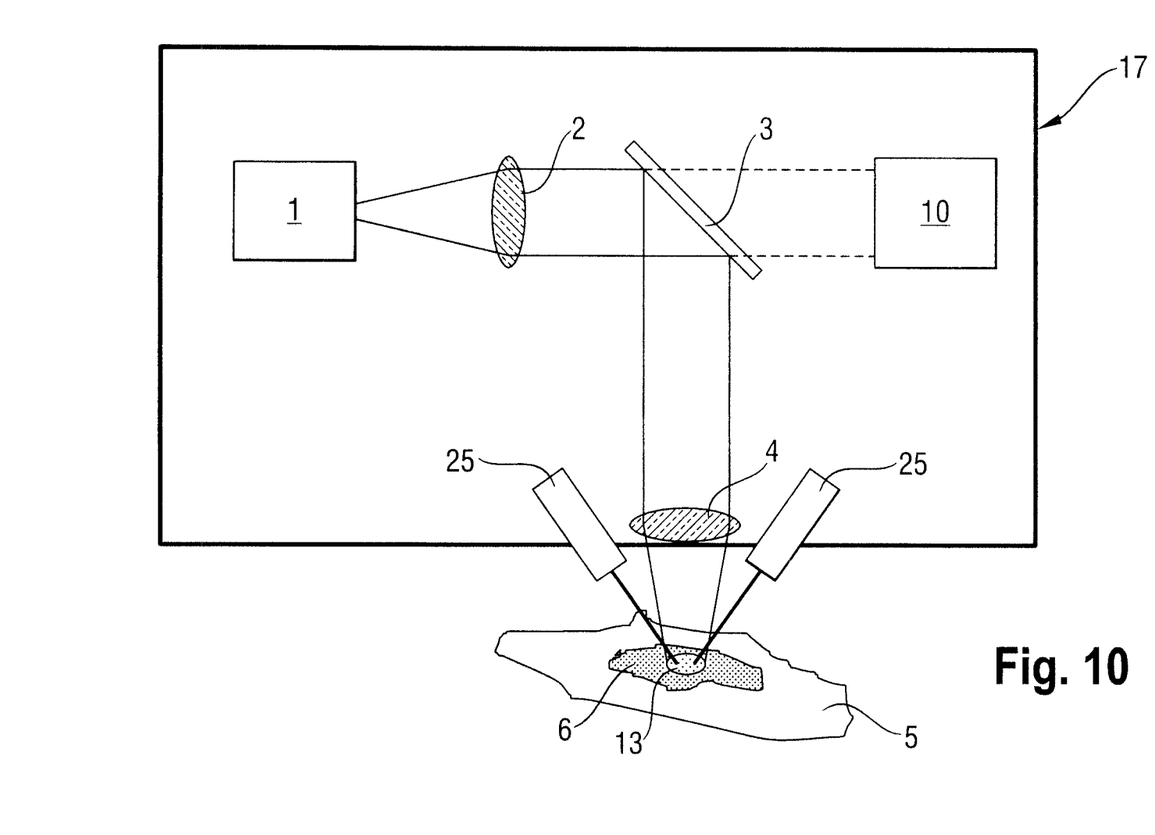
FIG. 10 a centering of irradiation means.

In the following, embodiments according to FIG. 10 will be elucidated:

FIG. 10 shows two light-sources 25 which, in particular, may take the form of laser diodes. These beams are likewise directed towards the irradiation region 13 (FIG. 10). They serve for spatial adjustment and, in particular, centering of the system. The radiation of the light-sources 25, which is reflected from the tissue 5, can, for example, be separated on the basis of the wavelengths via the lens and the partially transmitting mirror 3 and can be evaluated with a camera system (at the location of the block 9), in order to enable a spatial adjustment of the radiation. For this purpose, in particular the beam directed towards the tissue 5 via the lens 4 and the aligning beam of at least one of the light-sources 25 in the set condition are concentric. The angle at which the beam of the at least one light-source 25 (in FIG. 10 two are shown) impinges on the tissue 5 is predetermined and known precisely.

Figure 8:
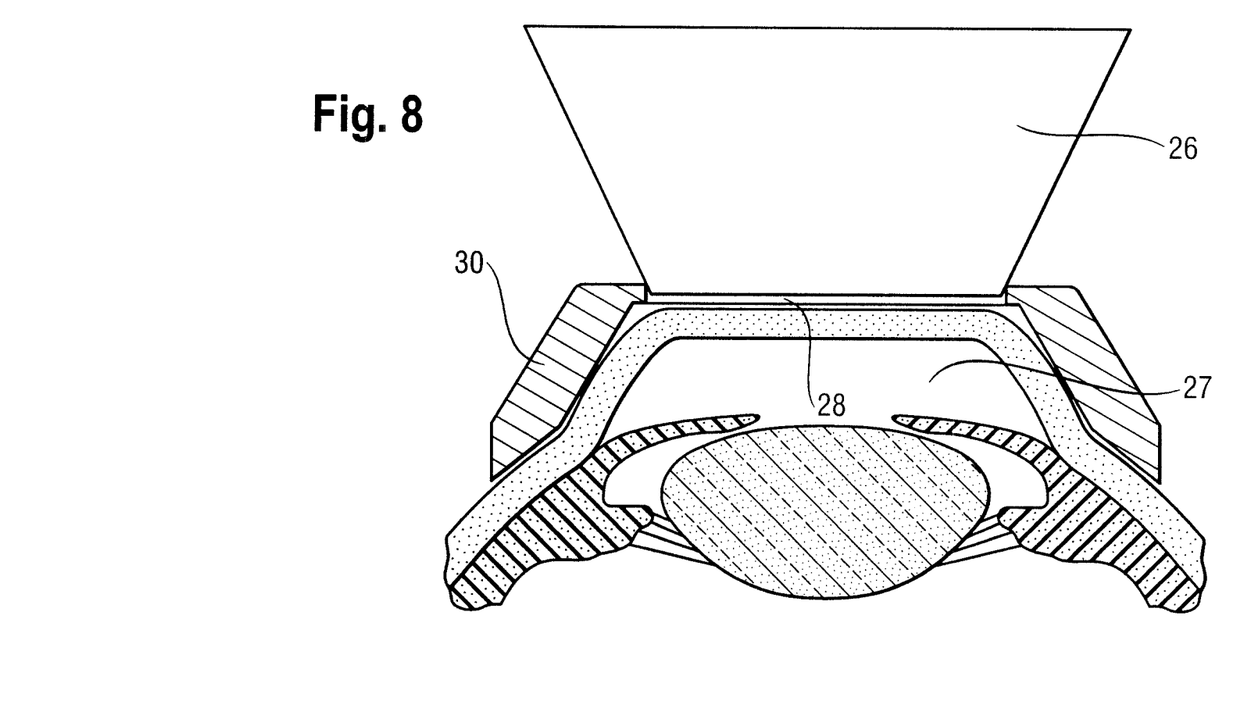
FIG. 8 a further embodiment of an adapter, similar to FIG. 7.
Figure 9:
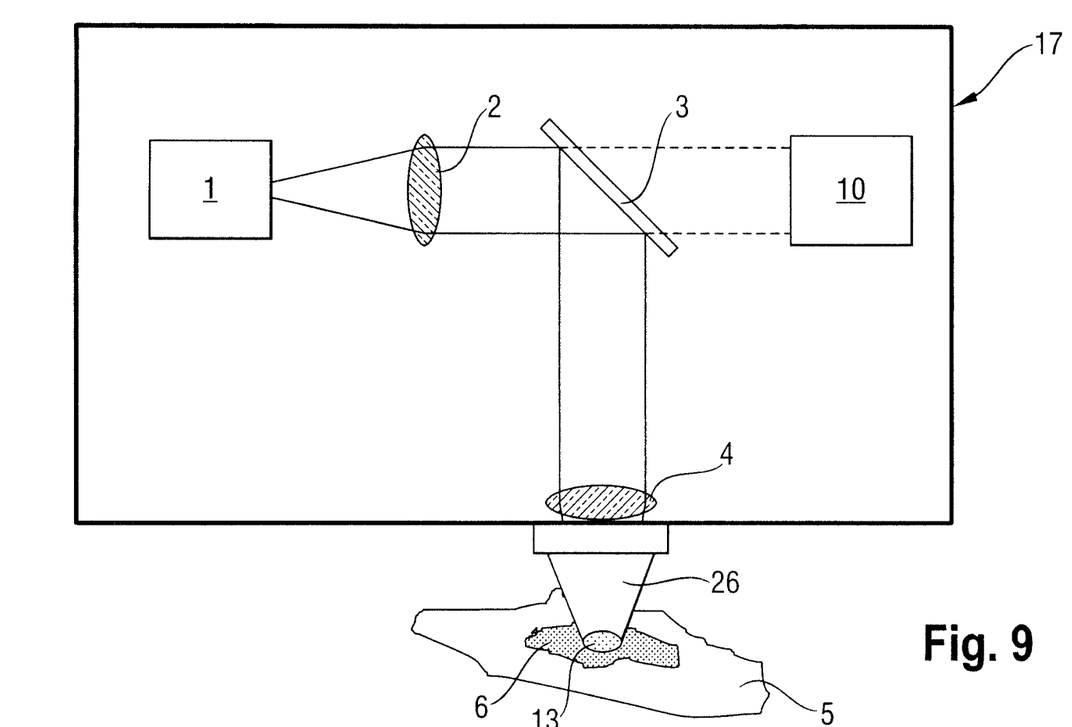
FIG. 9 the interaction of a medical radiation system with an adapter.

Some details of a device for positioning the irradiation system in relation to an eye to be treated will be elucidated in the following with reference to FIGS. 7 through 9.

Figure 7:
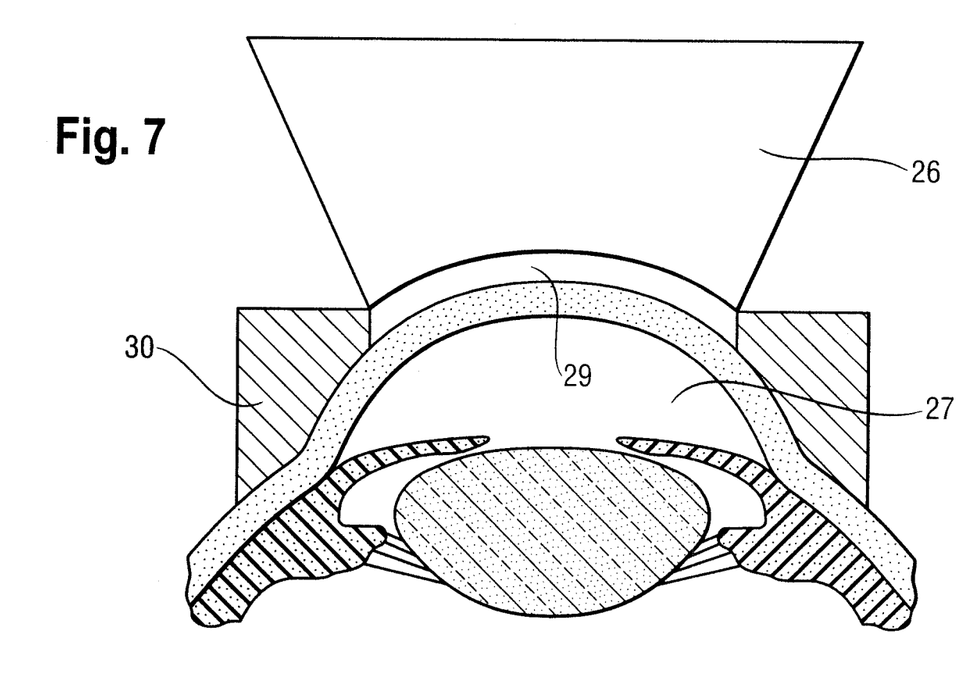
FIG. 7 schematically, an adapter for an irradiation system of the aforementioned type for the purpose of positioning in relation to an eye.

The irradiation unit 17 is positioned in relation to the eye via an adapter 26 (FIG. 7). FIGS. 7 and 8 show the component parts of the eye 27 schematically. The adapter 26 has a face-shaped shell overall, so that movements of the eye during the irradiation are prevented.

The adapter 26 has, moreover, an applanation mould 29, 28 (cf. FIG. 7, FIG. 8) which is transparent in respect of the radiation that is used and, where appropriate, reflected. The applanation mould 28 is pressed onto the cornea and deforms the cornea in desired manner. For example, the shape of the applanation mould 28 may be—corresponding to the diagnosis—spherical, aspherical bitoric, or described by a Zernike polynomial. The Zernike polynomial may extend to the $10^{th}$ order.

The applicator 26, which encloses and supports the cornea all around, may, according to one embodiment, be provided with means in order to deliver the medicament to be injected into the tissue, specifically in defined doses. In the applicator a small pump may be provided which is capable of being driven electrically by the controller 7, in order to transfer the medicament into the cornea.

The applanation mould of the adapter 26—that is to say, the mould with which the adapter shapes the tissue to be treated, that is to say, in particular, the cornea, by gentle pressing—may be configured in such a way that the tissue is shaped only in parts—that is to say, in certain selected regions. These shaped regions may lie inside and/or outside the irradiated zone. FIG. 9 illustrates an example interaction of a medical irradiation system 17 and the adapter 26.

The mechanical adapter 26 may exhibit sensors, the arrangement of which is indicated by reference symbol 30. For example, the sensors can ascertain biomechanical properties of the tissue. The sensors 30 may also be provided in order to ascertain the concentration of the chemical active substance in the tissue.

The sensors 30 may also be designed in order to ascertain an active-substance concentration in the anterior chamber of the eye.

Overall, the adapter 26 may be provided with a mechanical suction apparatus with respect to the eye 27. In this case a sensor may be provided, in order to measure the pressing force on the eye and to pass a corresponding signal to the controller 7.

The adapter 26 may also be provided with a mechanical system in order to remove the epithelium of the tissue.

Figure 5:
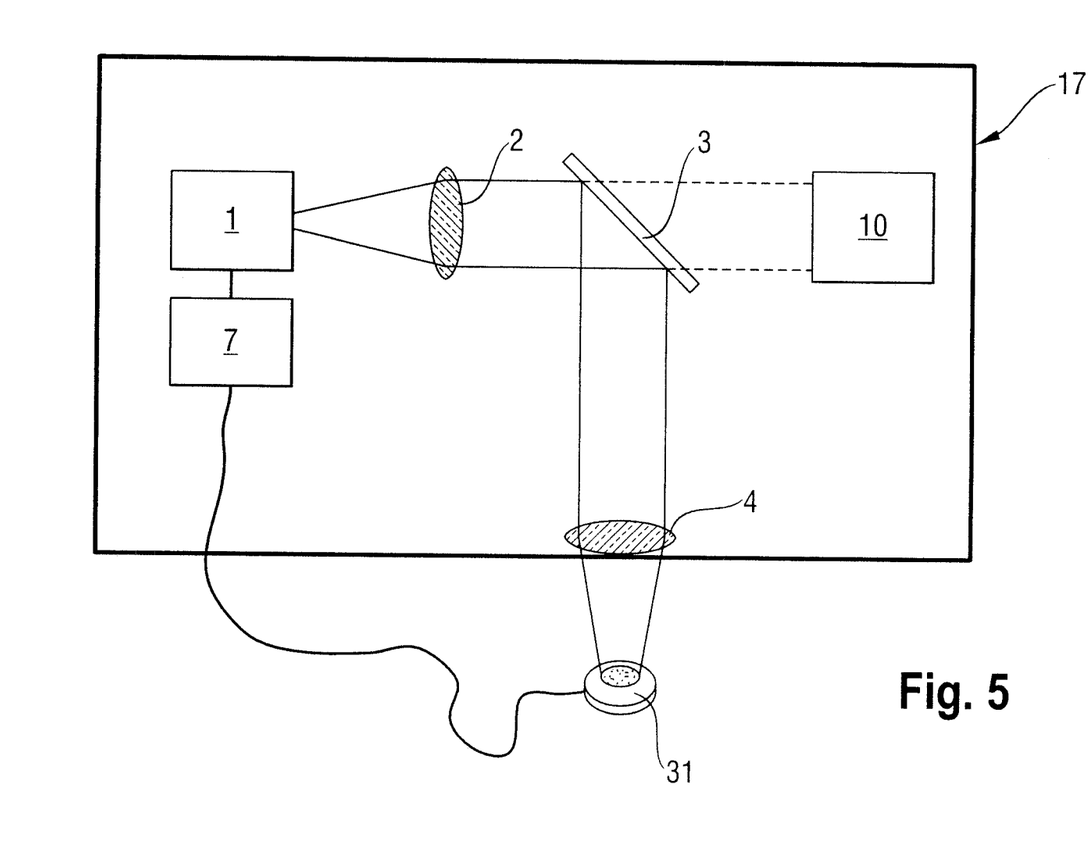
FIG. 5 a further detail of an irradiation system for medical purposes, with a calibrating device.

An external calibration system will be described in the following, in particular with regard to FIG. 5:

In the arrangement according to FIG. 5, an irradiation unit 17 is represented as regards its components of interest here (otherwise it corresponds to FIG. 1), without interacting with an eye to be treated. The eye has been replaced by a calibration means 31. With the calibration system 31 the functioning of the irradiation system is tested before it comes into operation on the eye.

The calibration means 31 may be, for example, an energy sensor, a spectrometer, a beam-profile camera, a time-measuring device, a photometer, or a fluorescent medium in respect of the active radiation. The calibration means 31 supplies signals to the controller 7, so that a closed control loop with respect to the radiation emitted via the radiation source 1 is capable of being generated via the controller.

The calibration means 31 may also be integrated into the applicator and may then be employed during the treatment.

Figure 6:
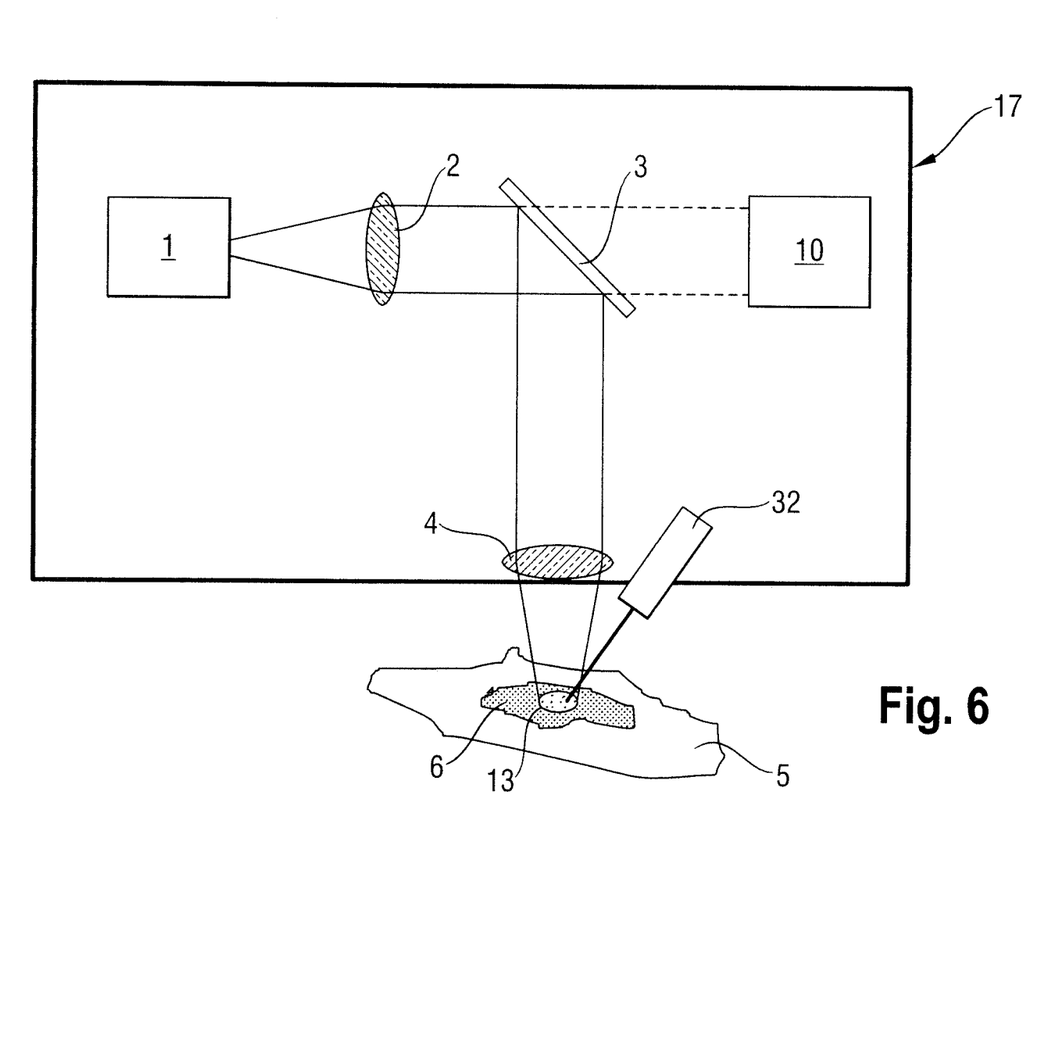
FIG. 6 a further detail of an irradiation system for medical purposes.

An applicator 32 for medicaments will be described in the following with regard to FIG. 6:

According to FIG. 6, an applicator 32 for medicaments is arranged close to the irradiation area 13 on or in the tissue to be treated. The applicator 32 may be an injector, a drip system or a spray system. The applicator 32 may also be controlled as regards its delivery of medicaments via the controller.

Control of the applicator 32 via the controller 7 can preferably be effected in combination with a diagnosis during the treatment by means of the diagnostic means arranged in the block 9—that is to say, in the form of a closed control loop.

Figure 4:
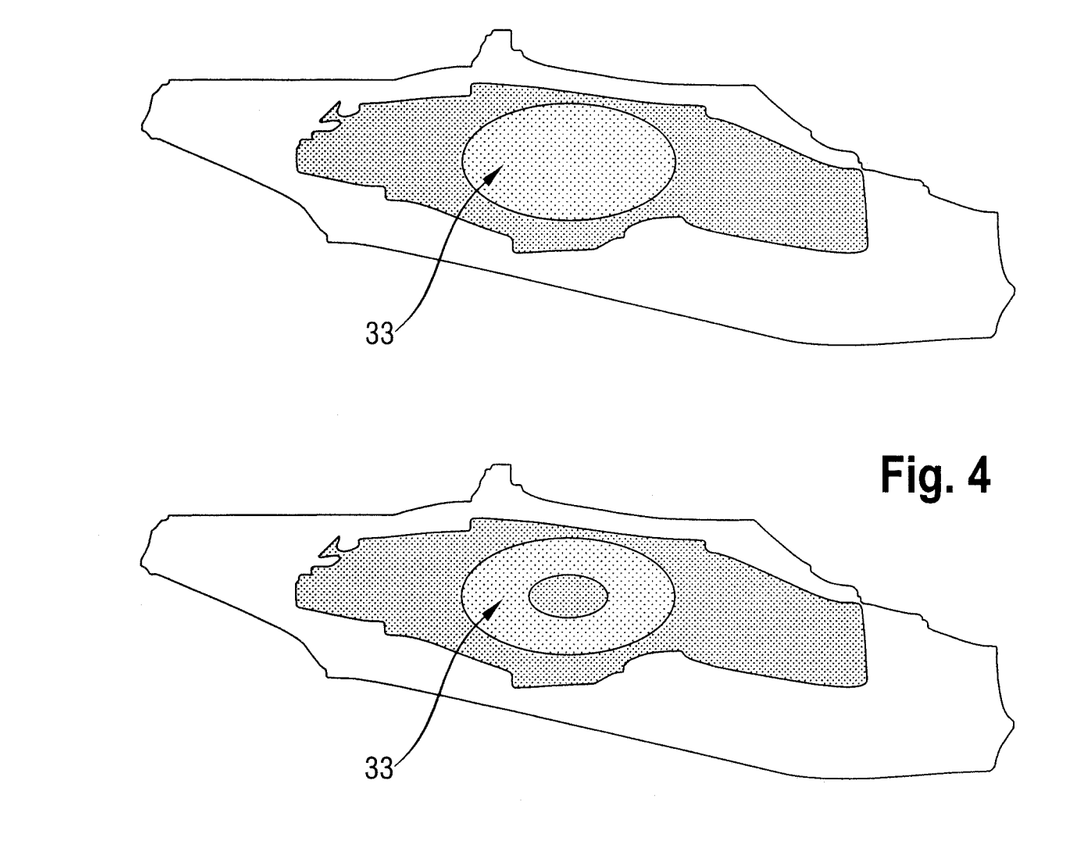
FIG. 4 schematically, embodiments of irradiation fields.

FIG. 4 shows special configurations of the irradiation of the tissue. The irradiation region 13 may accordingly exhibit, for example, the special configurations 33 shown in FIG. 4—that is to say, for example, a closed circular shape according to FIG. 4, top, or an annular shape according to FIG. 4, bottom. An elliptical shape with defined eccentricity may also be chosen for the irradiation field. The stated light shapes may also be combined—for example, in temporal succession—depending on the diagnosis.

The invention claimed is:

1. An irradiation system for irradiating a cornea of a patient, the system comprising:
    a) at least one radiation source (1) emitting a primary radiation within the range of wavelengths from 300 nm to 800 nm, which radiation causes in the irradiated cornea (5) photochemically a change in the biomechanical properties of the cornea but no photoablative effect;
    b) an optical system comprising at least two lenses (2, 4) to direct the radiation towards the cornea to be irradiated, wherein means (7) are provided to adjust a temporally and spatially variable intensity distribution of the radiation;
    c) at least one diaphragm (12) which confines the radiation to an irradiation region (13) of the cornea;
    d) at least one beam-splitter (3) which couples out a part of the radiation for monitoring purposes by means of radiation detector (10), wherein said beam splitter also brings said primary radiation together with a secondary radiation of a different wavelength from a secondary radiation source;
    e) a sensor for sensing one of the group including the current consumption of the radiation source, a temperature of one or more components of the system, a temperature of an environment of the system, and an atmospheric humidity;
    f) a controller (7) receiving data from said sensor in accordance with said sensed current or temperature or, humidity and for controlling the at least one radiation source in accordance with said received data;
    g) a mechanical stand (16) for positioning the at least one radiation source, the optical system, the at least one diaphragm, the at least one beam splitter, the sensor and the controller in relation to the cornea (5) to be irradiated;
    h) an electronic interface (8) between said controller (7) and an external computer for the purpose of transmitting data selected from the group comprising duration of irradiation, dose of irradiation, and light distribution; and
    i) an interface (19) for the input of data by a user, said data being selected from irradiation time and irradiation dose.

2. The irradiation system according to claim 1, wherein a diffractive element or a holographic element (20) is arranged in said optical system.

3. The irradiation system according to claim 1 comprising a light modulator in a beam path of said radiation for modulating a light distribution in said irradiation region (13).

4. The irradiation system according to claim 1, wherein said diaphragm (12) is electronically controllable to adjust its diaphragm aperture.

5. The irradiation system according to claim 1 comprising an optical coherence tomography device (9) arranged behind said beam splitter(3) to receive radiation reradiated from the cornea (5).

6. The irradiation system according to claim 1 comprising a device (9) for measuring a wavelength that is reradiated from the cornea (5).

7. The irradiation system according to claim 1 further comprising an adapter (26) which is applied to the cornea (5) for shaping the cornea.

8. The irradiation system according to claim 1 further comprising a sensor for detecting fluorescence radiation, wherein said sensor is arranged behind said beam splitter (3) to receive radiation reradiated from the cornea.

9. The irradiation system according to claim 1 further comprising with means (25) for adjusting and centering the radiation.

10. The irradiation system according to claim 1 further comprising with an adapter (26) for aligning the irradiation system and shaping the tissue to be irradiated.

11. The irradiation system according to claim 1 further comprising with an external calibration system (31).

\* \* \* \* \*